United States Patent
Mu et al.

(10) Patent No.: US 12,098,402 B2
(45) Date of Patent: Sep. 24, 2024

(54) CONSTRUCTION METHOD AND APPLICATION OF MICROORGANISM CAPABLE OF REALIZING HIGH PRODUCTION OF LACTO-N-NEOTETRAOSE

(71) Applicant: Jiangnan University, Wuxi (CN)

(72) Inventors: Wanmeng Mu, Wuxi (CN); Yingying Zhu, Wuxi (CN); Guocong Luo, Wuxi (CN); Wenli Zhang, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 18/485,543

(22) Filed: Oct. 12, 2023

(65) Prior Publication Data

US 2024/0035058 A1   Feb. 1, 2024

Related U.S. Application Data

(63) Continuation of application No. PCT/CN2022/110193, filed on Aug. 4, 2022.

(30) Foreign Application Priority Data

Aug. 6, 2021  (CN) .......................... 202110900122.6

(51) Int. Cl.
| | | |
|---|---|---|
| *C12P 19/04* | (2006.01) | |
| *C12N 1/20* | (2006.01) | |
| *C12N 9/10* | (2006.01) | |
| *C12N 9/90* | (2006.01) | |
| *C12N 15/70* | (2006.01) | |

(52) U.S. Cl.
CPC .............. *C12P 19/04* (2013.01); *C12N 1/205* (2021.05); *C12N 9/1051* (2013.01); *C12N 9/90* (2013.01); *C12N 15/70* (2013.01); *C12N 2500/34* (2013.01); *C12N 2500/35* (2013.01); *C12Y 204/01038* (2013.01); *C12Y 204/01146* (2013.01)

(58) Field of Classification Search
CPC ........ C12N 9/1051; C12N 1/205; C12P 19/04
See application file for complete search history.

(56) References Cited

FOREIGN PATENT DOCUMENTS

| CN | 108410787 A | 8/2018 | |
|---|---|---|---|
| CN | 111979168 A | 11/2020 | |
| CN | 112280727 A * | 1/2021 | ............. C12N 15/52 |
| CN | 113136357 A | 7/2021 | |
| CN | 113684164 A | 11/2021 | |
| EP | 3141610 A1 * | 3/2017 | ............. C07K 14/24 |
| EP | 3425052 A1 * | 1/2019 | ........... A23L 33/125 |
| WO | 2007023348 A2 | 3/2007 | |
| WO | 2015150328 A1 | 10/2015 | |

OTHER PUBLICATIONS

Priem, et al. Glycobiology, 2002, vol. 12, No. 4. pp. 235-240 (Year: 2002).*
Nedergaard, et al. Pathogens 2019, 8, 256, pp. 1-10 (Year: 2019).*
Logan, et al. Molecular Microbiology (2000) 35(5), pp. 1156-1167 (Year: 2000).*
Schuster, et al. Applied and Env. Microbiol. Nov. 2022 vol. 88 Issue 22, pp. 1-18 (Year: 2022).*
GenBank, "lipooligosaccharide biosynthesis protein lex-1 [Aggregatibacter actinomycetemcomitans NUM4039]", BAS48030. 1,Oct. 7, 2016.

* cited by examiner

*Primary Examiner* — Louise W Humphrey
*Assistant Examiner* — Jessica Faye Edwards
(74) *Attorney, Agent, or Firm* — IPRO, PLLC

(57) ABSTRACT

Disclosed are a construction method and application of a microorganism capable of realizing high production of lacto-N-neotetraose, belonging to the field of microbial genetic engineering. Coding genes of ß-1,3-acetyl glucosamine transferase, ß-1,4-galactosyl transferase and/or UDP-glucose 4 epimerase are over-expressed on the basis of a strain which is previously constructed by the team and is subjected to related-gene knockout, thus enabling the strain to have a synthesis capability of producing the lacto-N-neotetraose. The present disclosure accurately regulates the carbon flux of a metabolic pathway and relieves the metabolic stress by screening the high-efficiency ß-1,4-galactosyl transferase gene and regulating the expression of IgtA, Aa-ß-1,4-GalT and galE in a lacto-N-neotetraose synthesis pathway in a combined manner. In a shake flask experiment, the lacto-N-neotetraose production capacity of *Escherichia coli* is 0.91 g/L. The lacto-N-neotetraose yield in a 3 L fermentation tank reaches 12.14 g/L. Therefore, the microorganism has an industrial application prospect.

10 Claims, 3 Drawing Sheets

Specification includes a Sequence Listing.

```
                       SEQUENCE LISTING

Sequence total quantity: 19
SEQ ID NO: 1           moltype = DNA  length = 1005
FEATURE                Location/Qualifiers
source                 1..1005
                       mol_type = other DNA
                       organism = synthetic construct
SEQUENCE: 1
atgggccagc cgctggttag cgttctgatc tgcgcgtaca acgttgaaaa atatttcgcg   60
cagagcctgg cagctgttgt taaccagacc tggcgtaagc tggacattct gatcgttgat  120
gatggctcta ccgatggcac cctggcgatc gcgcagcgtt tccaggaaca ggacggtcgt  180
atccgtattc tggcgcagcc gcgtaactct ggtctgattc caagcctgaa catcggcctg  240
gatgaactgg cgaaaagcgg cggtggtggt gaatacatcg cgcgtaccga tgcggatgat  300
atcgcagctc cggattggat tgaaaaaatc gttggtgaaa tggaaaaaga tcgtagcatc  360
atcgcaatgg gcgcttggct ggaagtgctg tccgaagaaa aagatggcaa ccgtctggca  420
cgtcaccacg aacacgg taa aatctggaaa aaaccgaccc gtcacgaaga catcgcggat  480
ttcttcccat tcggcaaccc gattcacaac aacaccatga tcatgcgtcg ttccgtgatc  540
gatggcggcc tgcgttacaa caccgaacgt gattgggcag aagactatca gttctggtat  600
gatgtttcta aactgggtcg tctggcgtac tacccggaag cgctggttaa ataccgtctg  660
cacgctaacc aggttagctc caaatatagc atccgccagc acgaaatcgc tcagggtatc  720
cagaaaaccg cacgtaacga tttcctgcag tctatgggtt tcaaaacccg tttcgatagc  780
ctggaatacc gtcagattaa agcggttgcg tatgaactgc tggaaaaaca cctgccggaa  840
gaagattttg aactggcgcg tcgtttcctg taccagtgct tcaaacgtac cgatacgctg  900
ccggcgggcg cttggctgga tttcgcggcg gatgccgta tgcgtcgtct gttcaccctg  960
cgtcagtact tcggtatcct gcaccgtctg ctgaaaaacc gttaa              1005

SEQ ID NO: 2           moltype = DNA  length = 732
FEATURE                Location/Qualifiers
source                 1..732
                       mol_type = other DNA
                       organism = synthetic construct
SEQUENCE: 2
atgaacagca ccgaaaacaa aaactttgtg attagcatta gcaccgcgga acagcgccgc   60
aaccatatta ttgaacagtt tacccatcag aacattccgt ttgaattttt tgatgcgttt  120
accccgagcg ataaactgac cgatcatctg cagcgctatc tgccgaacgt ggcgaacgcg  180
gcgcagctga ccatgggcga aaaaggctgc ctgatgagcc attttatgct gtggaaaaaa  240
tgcattgatg aaaacctgga ttatattacc ctgtttgaag atgatattct gctgggcgaa  300
aacgcgaaca aatttctggc ggaaggcgat tggctgaaag tgcgctttaa ctttcaagaa  360
atttttgtgc tgcgcctgga aacctttctg atgccggtgc agctggaaaa acagacgcag  420
attccgccgt ttcagcagcg cgatattgat attctgacga gcaaacattt tggcaccgcg  480
ggctatgtga ttagccaagg cgcggcgaaa tatctgattg cgctgtttga aaaactgacc  540
accgaagaaa ttaaaccgat tgatgaaatt atgtttaatc agcagattaa cgcgaccgat  600
tatcgcgtgt atcagctgaa cccggcgatt tgcgtgcaag aactgcagct gaaccaagaa  660
gcgagcctgc tggtgagcaa cctggaacaa gaacgcaaaa ttaacctgaa atatgaaaaa  720
cgcaaacatt aa                                                  732
```

```
SEQ ID NO: 3              moltype = DNA   length = 1017
FEATURE                   Location/Qualifiers
source                    1..1017
                          mol_type = other DNA
                          organism = synthetic construct
SEQUENCE: 3
atgagagttc tggttaccgg tggtagcggt tacattggaa gtcatacctg tgtgcaatta    60
ctgcaaaacg gtcatgatgt catcattctt gataacctct gtaacagtaa gcgcagcgta   120
ctgcctgtta tcgagcgttt aggcggcaaa catccaacgt ttgttgaagg cgatattcgt   180
aacgaagcgt tgatgaccga gatcctgcac gatcacgcta tcgacaccgt gatccacttc   240
gccgggctga agccgtggga cgaatcggta caaaaaccgc tggaatatta cgacaacaat   300
gtcaacggca ctctgcgcct gattagcgcc atgcgcgccg ctaacgtcaa aaactttatt   360
tttagctcct ccgccaccgt ttatggcgat cagcccaaaa ttccatacgt tgaaagctgc   420
ccgaccggca caccgaaaag cccttacggc aaaagcaagc tgatggtgga acagatcctc   480
accgatctgc aaaaagccca gccggactgg agcattgccc tgctcgcgta cttcaacccg   540
gttggcgcgc atccgtcggg cgatatgggc gaagatccgc aaggcattcc gaataacctg   600
atgccataca tcgcccaggt tgctgtaggc cgtcgcgact cgctggcgat tttggtaac    660
gattatccga ccgaagatgg tactggcgta cgcgattaca tccacgtaat ggatctggcg   720
gacggtcacg tcgtggcgat ggaaaaactg gcgaacaagc aggcgtaca catctacaac    780
ctcggcgctg gcgtaggcaa cagcgtgctg acgtggttaa tgccttcag caaagcctgc   840
ggcaaaccgg ttaattatca ttttgcaccg cgtcgcgagg cgaccttcc tgcctactgg    900
gcggacgcca gcaaagccga ccgtgaactg aactggcgcg taacgcgcac actcgatgaa   960
atggcgcagg acacctggca ctggcagtca cgccatccac agggatatcc cgattaa    1017

SEQ ID NO: 4              moltype = AA   length = 243
FEATURE                   Location/Qualifiers
source                    1..243
                          mol_type = protein
                          organism = Aggregatibacter actinomycetemcomitans
SEQUENCE: 4
MNSTENKNFV ISISTAEQRR NHIIEQFTHQ NIPFEFFDAF TPSDKLTDHL QRYLPNVANA    60
AQLTMGEKGC LMSHFMLWKK CIDENLDYIT LFEDDILLGE NANKFLAEGD WLKVRFNFQE   120
IFVLRLETFL MPVQLEKQTQ IPPFQQRDID ILTSKHFGTA GYVISQGAAK YLIALFEKLT   180
TEEIKPIDEI MFNQQINATD YRVYQLNPAI CVQELQLNQE ASLLVSNLEQ ERKINLKYEK   240
RKH                                                                 243

SEQ ID NO: 5              moltype = AA   length = 376
FEATURE                   Location/Qualifiers
source                    1..376
                          mol_type = protein
                          organism = synthetic construct
SEQUENCE: 5
MKVLTVFGTR PEAIKMAPLV HALAKDPFFE AKVCVTAQHR EMLDQVLKLF SIVPDYDLNI    60
MQPGQGLTEI TCRILEGLKP ILAEFKPDVV LVHGDTTTTL ATSLAAFYQR IPVGHVEAGL   120
RTGDLYSPWP EEANRTLTGH LAMYHFSPTE TSRQNLLREN VADSRIFITG NTVIDALLWV   180
RDQVMSSDKL RSELAANYPF IDPDKKMILV TGHRRESFGR GFEEICHALA DIATTHQDIQ   240
IVYPVHLNPN VREPVNRILG HVKNVILIDP QEYLPFVWLM NHAWLILTDS GGIQEEAPSL   300
GKPVLVMRDT TERPEAVTAG TVRLVGTDKQ RIVEEVTRLL KDENEYQAMS RAHNPYGDGQ   360
ACSRILEALK NNRISL                                                   376

SEQ ID NO: 6              moltype = AA   length = 266
FEATURE                   Location/Qualifiers
source                    1..266
                          mol_type = protein
                          organism = synthetic construct
SEQUENCE: 6
MRLIPLTTAE QVGKWAARHI VNRINAFKPT ADRPFVLGLP TGGTPMTTYK ALVEMHKAGQ    60
VSFKHVVTFN MDEYVGLPKE HPESYYSFMH RNFFDHVDIP AENINLLNGN APDIDAECRQ   120
YEEKIRSYGK IHLFMGGVGN DGHIAFNEPA SSLASRTRIK TLTHDTRVAN SRFFDNDVNQ   180
VPKYALTVGV GTLLDAEEVM ILVLGSQKAL ALQAAVEGCV NHMWTISCLQ LHPKAIMVCD   240
EPSTMELKVK TLRYFNELEA ENIKGL                                        266

SEQ ID NO: 7              moltype = AA   length = 1024
FEATURE                   Location/Qualifiers
source                    1..1024
                          mol_type = protein
                          organism = synthetic construct
SEQUENCE: 7
MTMITDSLAV VLQRRDWENP GVTQLNRLAA HPPFASWRNS EEARTDRPSQ QLRSLNGEWR    60
FAWFPAPEAV PESWLECDLP EADTVVVPSN WQMHGYDAPI YTNVTYPITV NPPFVPTENP   120
TGCYSLTFNV DESWLQEGQT RIIFDGVNSA FHLWCNGRWV GYGQDSRLPS EFDLSAFLRA   180
GENRLAVMVL RWSDGSYLED QDMWRMSGIF RDVSLLHKPT TQISDFHVAT RFNDDFSRAV   240
LEAEVQMCGE LRDYLRVTVS LWQGETQVAS GTAPFGGEII DERGGYADRV TLRLNVENPK   300
LWSAEIPNLY RAVVELHTAD GTLIEAEACD VGFREVRIEN GLLLLNGKPL LIRGVNRHEH   360
HPLHGQVMDE QTMVQDILLM KQNNFNAVRC SHYPNHPLWY TLCDRYGLYV VDEANIETHG   420
MVPMNRLTDD PRWLPAMSER VTRMVQRDRN HPSVIIWSLG NESGHGANHD ALYRWIKSVD   480
PSRPVQYEGG GADTTATDII CPMYARVDED QPFPAVPKWS IKKWLSLPGE TRPLILCEYA   540
HAMGNSLGGF AKYWQAFRQY PRLQGGFVWD WVDQSLIKYD ENGNPWSAYG GDFGDTPNDR   600
```

```
QFCMNGLVFA DRTPHPALTE AKHQQQFFQF RLSGQTIEVT SEYLFRHSDN ELLHWMVALD    660
GKPLASGEVP LDVAPQGKQL IELPELPQPE SAGQLWLTVR VVQPNATAWS EAGHISAWQQ    720
WRLAENLSVT LPAASHAIPH LTTSEMDFCI ELGNKRWQFN RQSGFLSQMW IGDKKQLLTP    780
LRDQFTRAPL DNDIGVSEAT RIDPNAWVER WKAAGHYQAE AALLQCTADT LADAVLITTA    840
HAWQHQGKTL FISRKTYRID GSGQMAITVD VEVASDTPHP ARIGLNCQLA QVAERVNWLG    900
LGPQENYPDR LTAACFDRWD LPLSDMYTPY VFPSENGLRC GTRELNYGPH QWRGDFQFNI    960
SRYSQQQLME TSHRHLLHAE EGTWLNIDGF HMGIGGDDSW SPSVSAEFQL SAGRYHYQLV   1020
WCQK                                                                1024

SEQ ID NO: 8            moltype = DNA   length = 36
FEATURE                 Location/Qualifiers
source                  1..36
                        mol_type = other DNA
                        organism = synthetic construct
SEQUENCE: 8
ctttaagaag gagatatacc atgggccagc cgctgg                               36

SEQ ID NO: 9            moltype = DNA   length = 40
FEATURE                 Location/Qualifiers
source                  1..40
                        mol_type = other DNA
                        organism = synthetic construct
SEQUENCE: 9
gcgccgagct cgaattctta acggtttttc agcagacggt                           40

SEQ ID NO: 10           moltype = DNA   length = 36
FEATURE                 Location/Qualifiers
source                  1..36
                        mol_type = other DNA
                        organism = synthetic construct
SEQUENCE: 10
tctgctgaaa aaccgttaag aattcgagct cggcgc                               36

SEQ ID NO: 11           moltype = DNA   length = 53
FEATURE                 Location/Qualifiers
source                  1..53
                        mol_type = other DNA
                        organism = synthetic construct
SEQUENCE: 11
ccagcggctg gcccatggta tatctccttc ttaaagttaa acaaaattat ttc            53

SEQ ID NO: 12           moltype = DNA   length = 51
FEATURE                 Location/Qualifiers
source                  1..51
                        mol_type = other DNA
                        organism = synthetic construct
SEQUENCE: 12
gatataccat gggcagcagc catatgaaca gcaccgaaaa caaaaacttt g              51

SEQ ID NO: 13           moltype = DNA   length = 60
FEATURE                 Location/Qualifiers
source                  1..60
                        mol_type = other DNA
                        organism = synthetic construct
SEQUENCE: 13
cctggctgtg gtgatgatgg tgttaatgtt tgcgtttttc atatttcagg ttaattttgc     60

SEQ ID NO: 14           moltype = DNA   length = 33
FEATURE                 Location/Qualifiers
source                  1..33
                        mol_type = other DNA
                        organism = synthetic construct
SEQUENCE: 14
ctcaattgga tgagagttct ggttaccggt ggt                                  33

SEQ ID NO: 15           moltype = DNA   length = 33
FEATURE                 Location/Qualifiers
source                  1..33
                        mol_type = other DNA
                        organism = synthetic construct
SEQUENCE: 15
ccgatattta atcgggatat ccctgtggat ggc                                  33

SEQ ID NO: 16           moltype = DNA   length = 34
FEATURE                 Location/Qualifiers
source                  1..34
                        mol_type = other DNA
                        organism = synthetic construct
```

```
SEQUENCE: 16
cgcaaacatt aacaccatca tcaccacagc cagg                                34

SEQ ID NO: 17           moltype = DNA  length = 57
FEATURE                 Location/Qualifiers
source                  1..57
                        mol_type = other DNA
                        organism = synthetic construct
SEQUENCE: 17
accaccggta accagaactc tcatccaatt gagatctgcc atatgtatat ctccttc       57

SEQ ID NO: 18           moltype = DNA  length = 43
FEATURE                 Location/Qualifiers
source                  1..43
                        mol_type = other DNA
                        organism = synthetic construct
SEQUENCE: 18
gccatccaca gggatatccc gattaaatat cggccggcca cgc                      43

SEQ ID NO: 19           moltype = DNA  length = 47
FEATURE                 Location/Qualifiers
source                  1..47
                        mol_type = other DNA
                        organism = synthetic construct
SEQUENCE: 19
ggtgctgttc atatggctgc tgcccatggt atatctcctt attaaag                  47
```

CONSTRUCTION METHOD AND APPLICATION OF MICROORGANISM CAPABLE OF REALIZING HIGH PRODUCTION OF LACTO-N-NEOTETRAOSE

REFERENCE TO SEQUENCE LISTING

The instant application contains a Sequence Listing in XML format as a file named"YGHY-2022-82-SEQ.xml", created on Sep. 25, 2023, of 23 kB in size, and which is hereby incorporated by reference in its entirety.

TECHNICAL FIELD

The present disclosure relates to a construction method and application of a microorganism capable of realizing high production of lacto-N-neotetraose, belonging to the field of microbial genetic engineering.

BACKGROUND

Human milk is generally considered to be the most important source of nutrition for infants. As the third largest solid component in human milk after lactose and fat, the synthesis of human milk oligosaccharides plays an important role in the growth of beneficial intestinal flora in infants and the prevention of adhesion between pathogenic bacteria and epithelial cells. There are more than two hundred kinds of human milk oligosaccharides that have been reported, which are mainly divided into three categories, i.e., sialylated, fucosylated and non-fucosylated neutral human milk oligosaccharides, accounting for 12-14%, 35-50% and 42-55%, respectively. The highest proportion of non-fucosylated neutral human milk oligosaccharides mainly include lacto-N-tetrose and lacto-N-neotetraose, which respectively account for 6% of the total human milk oligosaccharides. A large amount of literature has concentrated on reporting that these two neutral tetrasaccharides have obvious promoting effects on the health of infants and young children, and both the lacto-N-tetrose and the lacto-N-neotetraose have been approved by the US FDA and EU as additives to infant milk powder, thus receiving widespread attention.

At present, the lacto-N-neotetraose can be obtained through chemical synthesis and biosynthesis. In contrast, biosynthesis is more suitable for large-scale industrial production due to its high specificity between enzymes and substrates, cheap substrates, simplified synthesis steps, fewer by-products, and greatly improved yield. Currently, microbial fermentation is mainly used to synthesize the lacto-N-neotetraose. The synthesis of the lacto-N-neotetraose by the microbial fermentation requires a key ß-1,4-galactosyl transferase capable of catalyzing the conversion of a precursor lacto-N-triose II. At present, only one *Neisseria meningitidis*-derived gene (IgtB) encoding the ß-1,4-galactosyl transferase has been studied and applied to the production of the lacto-N-neotetraose. Recently, *Bacillus subtilis* was engineered to produce the lacto-N-neotetraose (LNnT) by chromosomal integration of two key genes, i.e., a gene IgtA (encoding ß-1,3-N-acetyl glucosamine transferase) and a gene IgtB. After optimization steps, an engineered strain simultaneously produced the lacto-N-neotetraose (LNnT) and the lacto-N-triose II, and the titers thereof in batch culture were 4.52-5.41 g/L and 2.64-2.98 g/L, respectively (Dong X M, Li N, Liu Z M, et al. Modular pathway engineering of key precursor supply pathways for lacto-N-neotetraose production in *Bacillus subtilis*. Biotechnol Biofuels. 2019; 12(1):212, and Dong X M, Li N, Liu Z M, et al. CRISPRi-Guided multiplexed fine-tuning of metabolic flux for enhanced lacto-N-neotetraose production in *Bacillus subtilis*. J Agric Food Chem. 2020; 68(8): 2477-2484.). Therefore, it is necessary to create more efficient production strains to meet the requirements of industrialization.

SUMMARY

The inventors have screened a ß-1,4-galactosyl transferase derived from *Aggregatibacter actinomycetemcomitans*, which uses lacto-N-triose II and UDP-galactose as substrates to produce lacto-N-neotetraose, thus significantly increasing the yield of the lacto-N-neotetraose.

The present disclosure provides a recombinant *Escherichia coli*, which expresses ß-1,4-galactosyl transferase derived from *Aggregatibacter actinomycetemcomitans* NUM4039, β-1,3-acetyl glucosamine transferase derived from *Neisseria meningitidis*, and UDP-glucose 4 epimerase GalE derived from *E. coli*, and knocks out a gene encoding UDP-N-acetyl glucosamine-2-epimerase, a gene encoding glucosamine-6 phosphate deaminase, and a gene encoding ß-galactosidase; and the amino acid sequence of the ß-1,4-galactosyl transferase is as shown in SEQ ID NO.4.

In one implementation, a gene IgtA encoding the ß-1,3-acetyl glucosamine transferase is expressed by using a pACYCDuet-1, pCDFDuet-1, pRSFDuet-1, pCOLADuet-1 or pETDuet-1 vector, and a gene galE encoding the UDP-glucose 4 epimerase and a gene Aa-β-1,4-GalT encoding the ß-1,4-galactosyl transferase are co-expressed by using a pACYCDuet-1, pCDFDuet-1, pRSFDuet-1, pCOLADuet-1 or pETDuet-1 vector.

In one implementation, the gene IgtA encoding the ß-1,3-acetyl glucosamine transferase is expressed by using the pRSFDuet-1 vector, and the gene galE encoding the UDP-glucose 4 epimerase and the gene Aa-β-1,4-GalT encoding the ß-1,4-galactosyl transferase are simultaneously expressed by using the pRSFDuet-1 vector.

In one implementation, the gene IgtA encoding the ß-1,3-acetyl glucosamine transferase is expressed by using the pETDuet-1 vector, and the gene galE encoding the UDP-glucose 4 epimerase and the gene Aa-β-1,4-GalT encoding the ß-1,4-galactosyl transferase are simultaneously expressed by using the pRSFDuet-1 vector.

In one implementation, the gene IgtA encoding the ß-1,3-acetyl glucosamine transferase is expressed by using the pCDFDuet-1 vector, and the gene galE encoding the UDP-glucose 4 epimerase and the gene Aa-β-1,4-GalT encoding the ß-1,4-galactosyl transferase are expressed by using the pETDuet-1 vector.

In one implementation, the gene IgtA encoding the ß-1,3-acetyl glucosamine transferase is expressed by using the pACYCDuet-1 vector, and the gene galE encoding the UDP-glucose 4 epimerase and the gene Aa-β-1,4-GalT encoding the ß-1,4-galactosyl transferase are simultaneously expressed by using the pCOLADuet-1 vector.

In one implementation, the sequence of the gene IgtA of *N. meningitidis* is as shown in SEQ ID NO.1.

In one implementation, the nucleotide sequence of the gene Aa-β-1,4-GalT encoding the ß-1,4-galactosyl transferase is as shown in SEQ ID NO.2.

In one implementation, the gene galE encoding the UDP-glucose 4 epimerase is derived from *E. coli* K-12, and the nucleotide sequence of the gene galE is as shown in SEQ ID NO.3.

In one implementation, the NCBI sequence number of the UDP-N-acetyl glucosamine-2-epimerase WecB is YP_026253.1 (SEQ ID NO.5), the NCBI sequence number of the glucosamine-6 phosphate deaminase NagB is NP_415204.1 (SEQ ID NO.6), and the NCBI sequence number of the 6-galactosidase LacZ is NP_414878.1 (SEQ ID NO.7).

In one implementation, the *E. coli* includes, but is not limited to, *E. coli* BL21 (DE3).

The present disclosure provides a method for producing lacto-N-neotetraose, which uses the recombinant *E. coli* to fermentatively produce the lacto-N-neotetraose.

In one implementation, the recombinant *E. coli* is cultured under the conditions of 35-40° C. and 180-220 rpm to obtain seed liquid, and the seed liquid is added to a fermentation system containing glycerin in an amount of 2-5% and cultured until $OD_{600}$ is 0.6-0.8; and IPTG and lactose are added, the concentrations of the IPTG and the lactose in the reaction system are enabled to be 0.1-0.5 mM and 3-5 g/L, respectively, and induction culture is carried out for no less than 90 h.

In one implementation, the recombinant *E. coli* is cultured under the conditions of 37° C. and 200 rpm to obtain seed liquid, and the seed liquid is added to a fermentation system containing glycerin in an amount of 5% and cultured until $OD_{600}$ is 0.6-0.8; and IPTG and lactose are added, the concentrations of the IPTG and the lactose in the reaction system are enabled to be 0.2 mM and 5 g/L, respectively, and induction culture is carried out for 96 h.

In one implementation, the recombinant *E. coli* is cultured under the conditions of 35-40° C. and 180-220 rpm to obtain seed liquid, and the seed liquid is added to a fermentation system in an amount of 5-10% and cultured until $OD_{600}$ is 17±3; and IPTG and lactose are added, the concentrations of the IPTG and the lactose in the reaction system are enabled to be mM and 5-10 g/L, respectively, and induction culture is carried out for no less than 45 h.

In one implementation, the recombinant *E. coli* is cultured under the conditions of 37° C. and 200 rpm to obtain seed liquid, and the seed liquid is added to a fermentation system in an amount of 10% and cultured until $OD_{600}$ is 17±3; and IPTG and lactose are added, the concentrations of the IPTG and the lactose in the reaction system are enabled to be 0.2 mM and 10 g/L, respectively, and induction culture is carried out for 47.5 h.

In one implementation, the lactose and glycerin are supplemented in the reaction process to maintain the concentrations of the glycerin and the lactose to be not less than 6 g/L and 5 g/L, respectively.

In one implementation, when the concentration of the glycerin in the reaction system is lower than 6 g/L, glycerin with a final concentration of 6 g/L is added at once; and when the concentration of the lactose in the reaction system is lower than 5 g/L, lactose with a final concentration of 5 g/L is added at once.

The present disclosure provides the application of the ß-1,4-galactosyl transferase, whose amino acid sequence is as shown in SEQ ID NO.4, in preparation of the lacto-N-neotetraose.

In one implementation, the ß-1,4-galactosyl transferase is employed to produce the lacto-N-neotetraose in presence of the lacto-N-triose II and the UDP-galactose which are as substrates.

The present disclosure provides application of the recombinant *E. coli* in the fields of food, chemical industry and medicine.

The present disclosure provides application of the recombinant *E. coli* in preparation of the lacto-N-neotetraose and derivatives thereof.

The Beneficial Effects of the Present Disclosure

The present disclosure screens the high-efficiency ß-1,4-galactosyl transferase and applies same to fermentatively produce the lacto-N-neotetraose. On the basis of an *E. coli* host which is previously constructed by the team and is subjected to related-gene knockout, the IgtA encoding ß-1,3-acetyl glucosamine transferase gene and the screened gene Aa-β-1,4-GalT are over-expressed, the supply of a precursor UDP-galactose is enhanced, and the gene galE encoding UDP-glucose 4 epimerase is introduced, thus realizing the efficient production of the lacto-N-neotetraose. In a shake flask experiment, the lacto-N-neotetraose production capacity of the *E. coli* is 0.91 g/L. The lacto-N-neotetraose yield in a 3 L fermentation tank reaches 12.14 g/L. Therefore, the microorganism has an industrial application prospect.

DETAILED DESCRIPTION

Figure 1:
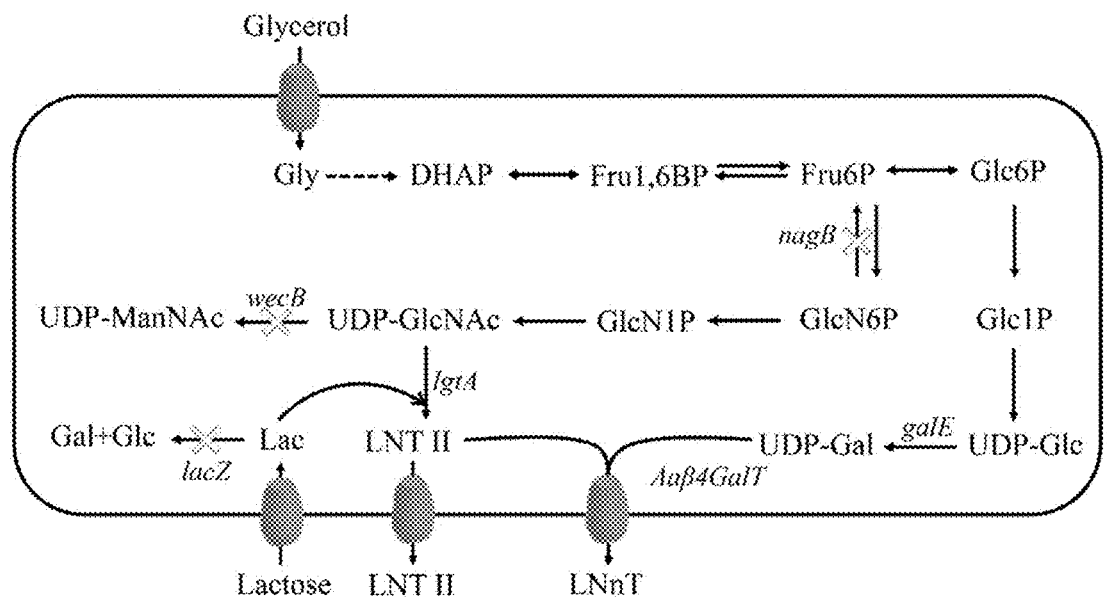
FIG. 1 is a diagram showing a metabolic pathway of lacto-N-neotetraose.

1. The plasmids, endonucleases, PCR enzymes, column DNA extraction kits, DNA gel recovery kits, and the like used in the following examples are commercial products, and the specific operations thereof are carried out in accordance with the kit instructions.

2. Colony PCR, nucleic acid agarose gel electrophoresis, protein SDS-PAGE gel electrophoresis, heat shock transformation, electrotransformation, preparation of competent cells, extraction and preservation of bacterial genomes, and other conventional operation methods are carried out based on Molecular Cloning: A Laboratory Manual (Fourth Edition).

3. The sequencing of plasmids and DNA products was entrusted to Shanghai Sangon Biotech Company for completion.

4. Preparation of competent *E. coli*: TAKARA kit.

5. Fermentation process and detection of lacto-N-tetrose (1) LB liquid medium: 10 g/L of peptone, 5 g/L of a yeast extract, and 10 g/L of sodium chloride.

(2) LB solid medium: 10 g/L of peptone, 5 g/L of yeast extract powder, 10 g/L of sodium chloride, and 15 g/L of agar powder.

(3) Fermentation medium: 20 g/L of glucose, 13.5 g/L of potassium dihydrogenphosphate, 4.0 g/L of diammonium hydrogenphosphate, 1.7 g/L of citric acid, 1.4 g/L of magnesium sulfate heptahydrate, and 10 ml/L of trace metal elements; and the trace metal elements include: 10 g/L of ferrous sulfate, 2.25 g/L of zinc sulfate heptahydrate, 1.0 g/L of anhydrous copper sulfate, 0.35 g/L of manganese sulfate monohydrate, 0.23 g/L of sodium borate decahydrate, 0.11 g/L of ammonium molybdate, and 2.0 g/L of calcium chloride dihydrate.

(4) The fermentation process of lacto-N-neotetraose: constructed strains were inoculated into the LB liquid medium and cultured overnight for 12 h under the conditions of 37°

C. and 200 rpm to obtain seed liquid; the seed liquid was inoculated into the 25 ml fermentation medium (containing 20 g/L glycerin) in an inoculation dosage of 2 mL/100 mL under the conditions of 37° C. and 200 rpm, and cultured until $OD_{600}$ is 0.6; and IPTG with a final concentration of 0.2 mM was added, 5 g/L lactose was added at the same time, and induction culture was continued for 96 h under the conditions of 25° C. and 200 rpm. 1 mL of fermentation broth was taken and centrifuged at 10,000 rpm for 10 min, and supernatant was extracted for HPLC determination.

(5) HPLC detection conditions: high-performance ion exchange chromatography; chromatographic column: CarboPac PA10 (4 mm×250 mm); detector: pulsed amperometric detector; mobile phase: A, ultrapure water; B, 1 M of sodium acetate; C, 250 mM of sodium hydroxide; flow rate: 1.0 mL/min; and injection volume: 20 μL.

Example 1: Construction of Recombinant Vector

The specific steps for constructing the recombinant expression vector were as follows (see Table 1 for primer sequences involved):
(1) Obtaining of IgtA Gene Fragments and Construction of Plasmids pAC-IgtA, pCO-IgtA, pCDF-IgtA, pET-IgtA, and pRSF-IgtA Under the conditions that the sequence of the gene IgtA of *N. meningitidis* (with a nucleotide sequence as shown in SEQ ID NO.1) was used as a template, and IgtA-F/R was used as a primer, PCR amplification was performed to amplify the IgtA gene fragments, and DNA fragments were collected by means of gel extraction. Under the conditions that IgtA-VF/R was used as a primer, and pRSFDuet-1, pETDuet-1, pCDFDuet-1, pCOLADuet-1 and pACYCDuet-1 vectors were used as templates, corresponding vector fragments were respectively amplified, and DNA fragments were collected by means of gel extraction.

The IgtA gene fragments amplified above were ligated to the corresponding vector fragments by means of a Gibson kit (produced by NEB Reagent Company, USA) to obtain the plasmids pRSF-IgtA, pET-IgtA, pCDF-IgtA, pCO-IgtA and pAC-IgtA, respectively.
(2) Obtaining of Aa-β-1,4-GalT and galE Gene Fragments and Construction of Plasmids pAC-Aa-galE, pCO-Aa-galE, pCDF-Aa-galE, pET-Aa-galE, and pRSF-Aa-galE A gene Aa-β-1,4-GalT was synthesized by Suzhou Jin-Weizhi through codon optimization (the nucleotide sequence was as shown in SEQ ID NO.2). Under the conditions that the synthesized gene was used as a template, and Aa-F/R was used as a primer, PCR amplification was performed to amplify an Aa-β1,4-GalT gene fragment, and DNA fragments were collected by means of gel extraction. Under the conditions that the genome of *E. coli* K-12 was used as a template, and Aa-GalE-F/R was used as a primer, PCR amplification was performed to amplify a galE gene fragment (the nucleotide sequence of a gene galE was as shown in SEQ ID NO.3), and DNA fragments were collected by means of gel extraction. Two pairs of primers, i.e., Aa-GalE-$V_1$-F/R and Aa-GalE-$V_2$-F/R, were used to amplify the plasmids pRSFDuet-1, pETDuet-1, pCDFDuet-1, pCOLADuet-1, and pACYCDuet-1, respectively, and DNA fragments were collected by means of gel extraction.

The Aa-β-1,4-GalT and galE gene fragments amplified above were ligated to the corresponding vector fragments by means of a Gibson kit (produced by NEB Reagent Company, USA) to obtain the plasmids pAC-Aa-galE, pCO-Aa-galE, pCDF-Aa-galE, pET-Aa-galE, and pRSF-Aa-galE, respectively.

TABLE 1

Primers for plasmid construction

| Primer name | Primer sequence (5'-3') |
|---|---|
| IgtA-F | CTTTAAGAAGGAGATATACCATGGGCCAGCCGCTGG (SEQ ID NO. 8) |
| IgtA-R | GCGCCGAGCTCGAATTCTTAACGGTTTTTCAGCAGA CGGT (SEQ ID NO. 9) |
| IgtA-V-F | TCTGCTGAAAAACCGTTAAGAATTCGAGCTCGGCGC (SEQ ID NO. 10) |
| IgtA-V-R | CCAGCGGCTGGCCCATGGTATATCTCCTTCTTAAAG TTAAACAAAATTATTTC (SEQ ID NO. 11) |
| Aa-F | GATATACCATGGGCAGCAGCCATATGAACAGCACCG AAAACAAAAACTTTG (SEQ ID NO. 12) |
| Aa-R | CCTGGCTGTGGTGATGATGGTGTTAATGTTTGCGTT TTTCATATTTCAGGTTAATTTTGC (SEQ ID NO. 13) |
| Aa-GalE-F | CTCAATTGGATGAGAGTTCTGGTTACCGGTGGT (SEQ ID NO. 14) |
| Aa-GalE-R | CCGATATTTAATCGGGATATCCCTGTGGATGGC (SEQ ID NO. 15) |
| Aa-GalE-$V_1$-F | CGCAAACATTAACACCATCATCACCACAGCCAGG (SEQ ID NO. 16) |
| Aa-GalE-$V_1$-R | ACCACCGGTAACCAGAACTCTCATCCAATTGAGATC TGCCATATGTATATCTCCTTC (SEQ ID NO. 17) |
| Aa-GalE-$V_2$-F | GCCATCCACAGGGATATCCCGATTAAATATCGGCCG GCCACGC (SEQ ID NO. 18) |
| Aa-GalE-$V_2$-R | GGTGCTGTTCATATGGCTGCTGCCCATGGTATATCT CCTTATTAAAG (SEQ ID NO. 19) |

Example 2: Construction of Recombinant Strains

A gene wecB encoding UDP-N-acetyl glucosamine-2-epimerase WecB (NCBI sequence number: YP_026253.1), a gene nagB encoding glucosamine-6 phosphate deaminase NagB (NCBI sequence number: NP_415204.1), and a gene lacZ encoding ß-galactosidase LacZ (NCBI sequence number: NP_414878.1) in *E. coli* BL21 were knocked out. For the gene knockout method, please refer to Patent Publication No. CN111979168A. Recombinant strains were constructed.

On the basis of the aforementioned recombinant strains, the recombinant plasmids constructed in Example 1 were transferred into the aforementioned recombinant strain of *E. coli* whose genes wecB, nagB, and lacZ were knocked out, and the key genes of lacto-N-neotetraose were expressed in a combined manner to obtain 18 different engineered strains, which were respectively denoted as EA1-18. The constructed recombinant strains are as shown in Table 2.

Example 3: Fermentation of Recombinant Strains to Produce lacto-N-neotetraose

Plasmid pRSFDuet-1 had a larger copy number, plasmid pETDuet-1 had a medium copy number, while plasmids pCDFDuet-1 and pCOLADuet-1 had smaller copy numbers, and plasmid pACYCDuet-1 had a minimum copy number. RSF, ColE1, CDF, ColA and P15A were replicons for expressing plasmids pRSFDuet-1, pETDuet-1, pCDFDuet-1, pCOLADuet-1 and pACYCDuet-1, respectively, representing different copy numbers, and the copy numbers of the five replicons were 100, 40, 20-40, 20-40 and 10-12, respectively.

The strains constructed in Example 2 were respectively inoculated into an LB liquid medium and cultured overnight for 12 h under the conditions of 37° C. and 200 rpm to obtain seed liquid; the seed liquid was inoculated into a 25 ml fermentation medium (containing 20 g/L glycerin) in an inoculation dosage of 2 mL/100 mL under the conditions of 37° C. and 200 rpm, and cultured until $OD_{600}$ is 0.6; and IPTG with a final concentration of 0.2 mM was added, g/L lactose was added at the same time, and induction culture was continued for 96 h under the conditions of 25° C. and 200 rpm. 1 mL of fermentation broth was taken and centrifuged at rpm for 10 min, and supernatant was extracted for HPLC determination.

Figure 2:
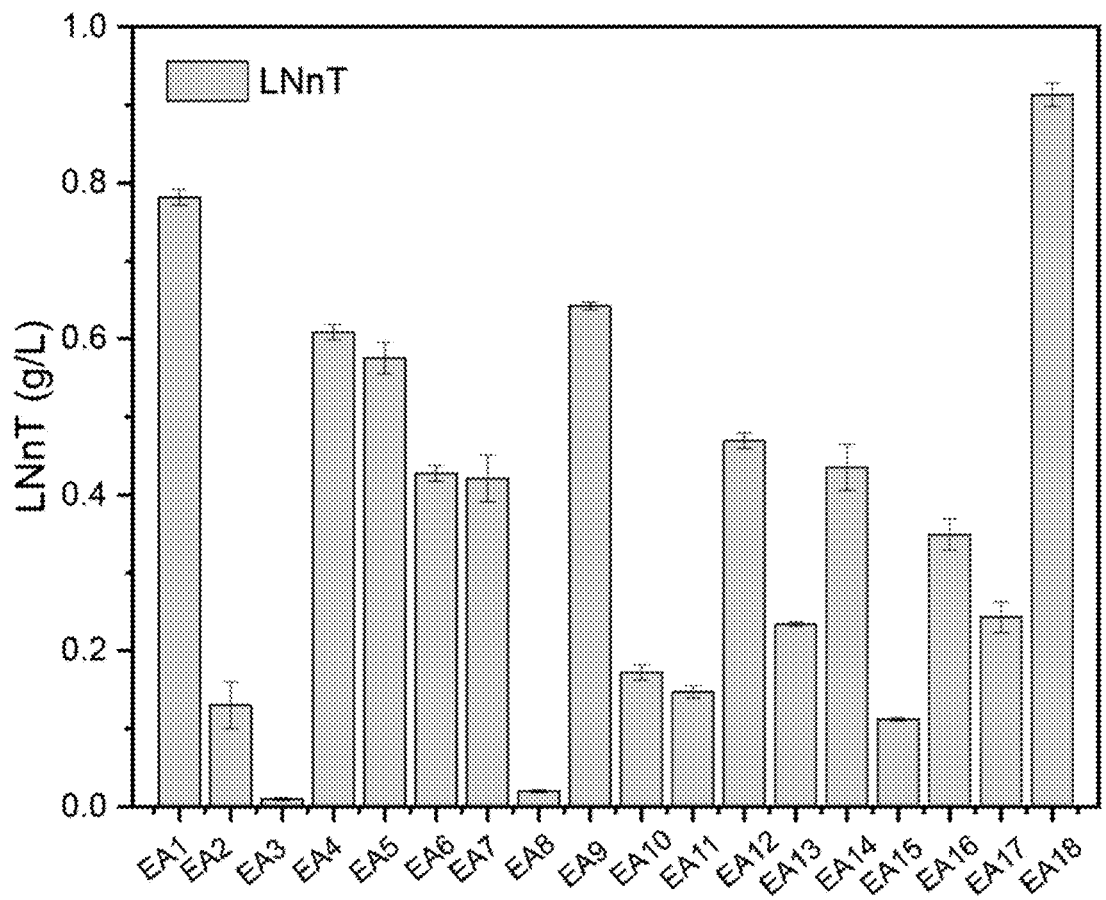
FIG. 2 is a diagram showing the yield of lacto-N-neotetraose under the regulation of different copy numbers of plasmids in a metabolic pathway.
Figure 3A:
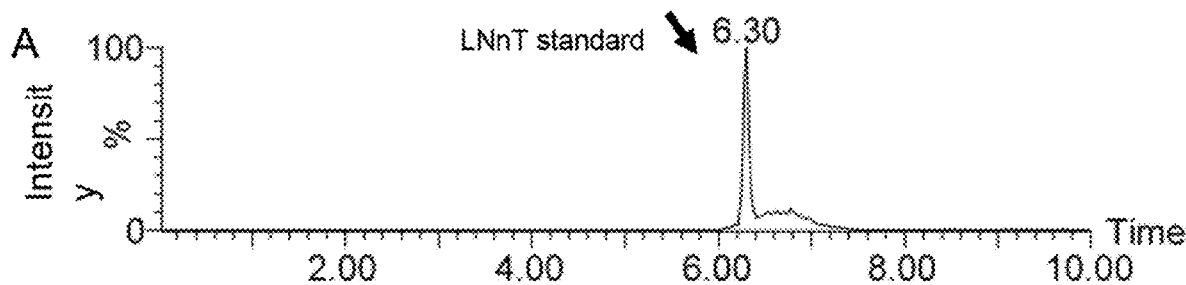
FIG. 3A to FIG. 3D are liquid phase diagrams and mass spectra of a lacto-N-neotetraose product standard sample and a lacto-N-neotetraose product sample.
Figure 3B:
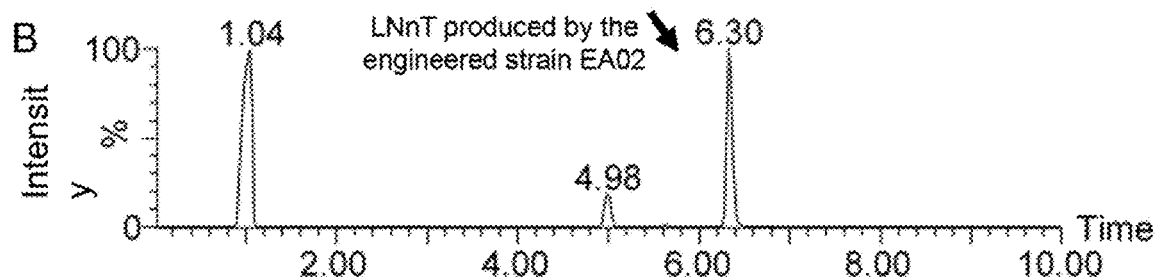
Figure 3C:
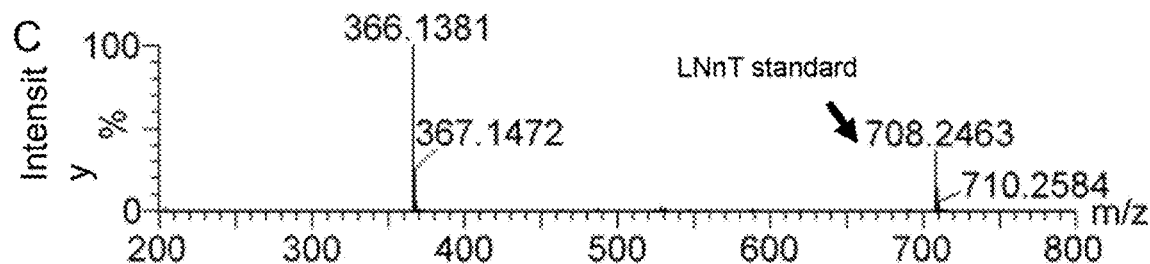
Figure 3D:
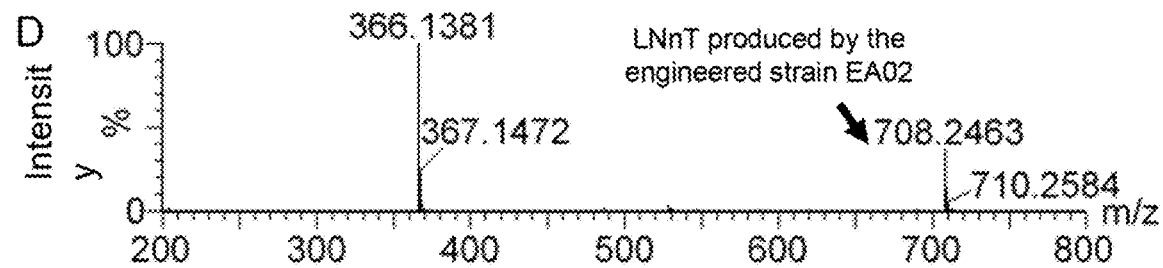

The results are as shown in Table 2: after fermentation, the lacto-N-neotetraose yields of the different engineered strains were 0.78 g/L, 0.13 g/L, 0.01 g/L, 0.61 g/L, 0.58 g/L, 0.43 g/L, g/L, 0.02 g/L, 0.64 g/L, 0.17 g/L, 0.15 g/L, 0.47 g/L, 0.23 g/L, 0.44 g/L, 0.11 g/L, 0.35 g/L, g/L, and 0.91 g/L, respectively. The engineered strain (i.e., strain EA18) containing the recombinant plasmids pAC-IgtA and pCO-Aa-galE obtained the highest yield of 0.91 g/L (see FIG. 2 for the lacto-N-neotetraose yields of all the engineered strains). Therefore, the gene IgtA expressing a relatively low gene dosage and the genes Aa-β-1,4-GalT and galE expressing a relatively high gene dosage can achieve higher lacto-N-neotetraose yields.

Example 4: Engineered Strain Fermentation Tank with Efficient Production to Produce lacto-N-neotetraose In order to further verify the effectiveness of the synthesis method of lacto-N-neotetraose and increase the lacto-N-neotetraose yield, the seed liquid of recombinant *E. coli* EA18 was inoculated into a fermentation medium with a working volume of 1 L in an inoculation dosage of 10%, where the fermentation temperature of a fermentation tank was 37° C., the stirring speed was 800 r/min, the ventilation volume was 1 vvm, and the pH was 7.0 (automatically controlled by supplementing ammonia water). Fermentation was performed for 12.5 h ($OD_{600}$ was approximately 17.6), lactose with a final concentration of 10 g/L and IPTG with a final concentration of 0.2 mM were added, and culturing was carried out at 25° C. During the culturing, glycerin and lactose were manually supplemented: when the concentration of the glycerin in the reaction system was below 6 g/L, 30 mL of mother liquor (600 g/L glycerin mother liquor) was added supplementarily, and when the concentration of the lactose was below 5 g/L, 25 ml of mother liquor (200 g/L lactose mother liquor) was added supplementarily, thus maintaining the growth of strains and the synthesis of lacto-N-neotetraose. After the entire culturing process

TABLE 2

Detailed information on shake flask fermentation of all engineered strains

Figure 4:
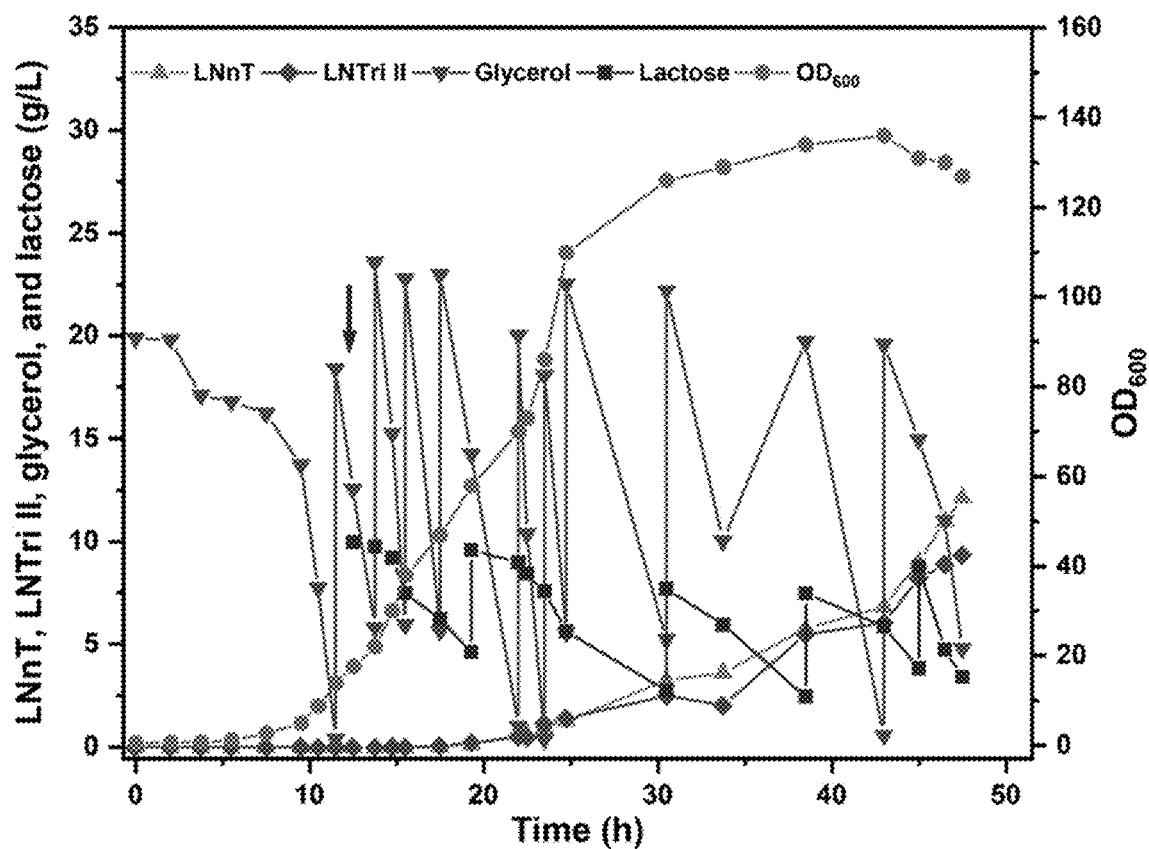
FIG. 4 is a resulting diagram showing the fermentation yield of lacto-N-neotetraose in a 3 L fermentation tank.

| Strain name | Plasmids contained in host, and genotype | Lacto-N-neotetraose yield (g/L) |
|---|---|---|
| EA1 | *E. coli* BL21 (DE3) whose genes wecB, nagB, and lacZ are knocked out, containing plasmids pRSF-lgtA and pET-Aa-galE | 0.78 |
| EA2 | *E. coli* BL21 (DE3) whose genes wecB, nagB, and lacZ are knocked out, containing plasmids pRSF-lgtA and pCDF-Aa-galE | 0.13 |
| EA3 | *E. coli* BL21 (DE3) whose genes wecB, nagB, and lacZ are knocked out, containing plasmids pRSF-lgtA and pAC-Aa-galE | 0.01 |
| EA4 | *E. coli* BL21 (DE3) whose genes wecB, nagB, and lacZ are knocked out, containing plasmids pET-lgtA and pRSF-Aa-galE | 0.61 |
| EA5 | *E. coli* BL21 (DE3) whose genes wecB, nagB, and lacZ are knocked out, containing plasmids pET-lgtA and pCDF-Aa-galE | 0.58 |
| EA6 | *E. coli* BL21 (DE3) whose genes wecB, nagB, and lacZ are knocked out, containing plasmids pET-lgtA and pCO-Aa-galE | 0.43 |
| EA7 | *E. coli* BL21 (DE3) whose genes wecB, nagB, and lacZ are knocked out, containing plasmids pET-lgtA and pAC-Aa-galE | 0.42 |
| EA8 | *E. coli* BL21 (DE3) whose genes wecB, nagB, and lacZ are knocked out, containing plasmids pCDF-lgtA and pRSF-Aa-galE | 0.02 |
| EA9 | *E. coli* BL21 (DE3) whose genes wecB, nagB, and lacZ are knocked out, containing plasmids pCDF-lgtA and pET-Aa-galE | 0.64 |
| EA10 | *E. coli* BL21 (DE3) whose genes wecB, nagB, and lacZ are knocked out, containing plasmids pCDF-lgtA and pCO-Aa-galE | 0.17 |
| EA11 | *E. coli* BL21 (DE3) whose genes wecB, nagB, and lacZ are knocked out, containing plasmids pCDF-lgtA and pAC-Aa-galE | 0.15 |
| EA12 | *E. coli* BL21 (DE3) whose genes wecB, nagB, and lacZ are knocked out, containing plasmids pCO-lgtA and pET-Aa-galE | 0.47 |
| EA13 | *E. coli* BL21 (DE3) whose genes wecB, nagB, and lacZ are knocked out, containing plasmids pCO-lgtA and pCDF-Aa-galE | 0.23 |
| EA14 | *E. coli* BL21 (DE3) whose genes wecB, nagB, and lacZ are knocked out, containing plasmids pCO-lgtA and pAC-Aa-galE | 0.44 |
| EA15 | *E. coli* BL21 (DE3) whose genes wecB, nagB, and lacZ are knocked out, containing plasmids pAC-lgtA and pRSF-Aa-galE | 0.11 |
| EA16 | *E. coli* BL21 (DE3) whose genes wecB, nagB, and lacZ are knocked out, containing plasmids pAC-lgtA and pET-Aa-galE | 0.35 |
| EA17 | *E. coli* BL21 (DE3) whose genes wecB, nagB, and lacZ are knocked out, containing plasmids pAC-lgtA and pCDF-Aa-galE | 0.24 |
| EA18 | *E. coli* BL21 (DE3) whose genes wecB, nagB, and lacZ are knocked out, containing plasmids pAC-lgtA and pCO-Aa-galE | 0.91 | reached 47.5 h, the $OD_{600}$ of the strains reached 127, and the yield of the lacto-N-neotetraose was the maximum, reaching up to 12.14 g/L (see FIG. 4).

TABLE 3

Dynamic changes in synthetic amount of strains and lacto-N-neotetraose during fermentation

| | Time (h) | | | | | | | | |
|---|---|---|---|---|---|---|---|---|---|
| | 11.5 | 12.5 | 17.5 | 22.5 | 25.75 | 33.75 | 38 | 45 | 47.5 |
| $OD_{600}$ | 14 | 17.6 | 47 | 73 | 112 | 129 | 134 | 131 | 127 |
| Lacto-N-neotetraose (g/L) | 0 | 0 | 0.03 | 0.63 | 1.69 | 3.61 | 5.76 | 9.0 | 12.14 |
| Lacto-N-triose II (g/L) | 0 | 0 | 0.07 | 0.48 | 1.71 | 2.04 | 5.46 | 8.2 | 9.36 |
| Glycerin (g/L) | 18.4 | 12.6 | 5.65 | 10.4 | 17.8 | 10.06 | 19.71 | 14.96 | 4.78 |
| Lactose (g/L) | 0 | 10 | 6.22 | 8.4 | 4.22 | 5.94 | 2.47 | 3.84 | 3.43 |

Although the present disclosure has been disclosed as above in exemplary examples, it is not intended to limit the present disclosure. Anyone familiar with this technology can make various changes and modifications without departing from the spirit and scope of the present disclosure. Therefore, the protection scope of the present disclosure shall be as defined in the Claims.

What is claimed is:

1. A recombinant *Escherichia coli*, wherein ß-1,4-galactosyl transferase derived from *Aggregatibacter actinomycetemcomitans* NUM4039, ß-1,3-acetyl glucosamine transferase derived from *Neisseria meningitidis*, and UDP-glucose 4 epimerase derived from *E. coli* are expressed, and a gene encoding UDP-N-acetyl glucosamine-2-epimerase, a gene encoding glucosamine-6 phosphate deaminase, and a gene encoding ß-galactosidase are knocked out; and the amino acid sequence of the ß-1,4-galactosyl transferase is as set forth in SEQ ID NO:4, and wherein the sequence of gene IgtA encoding the ß-1,3-acetyl glucosamine transferase of *N. meningitidis* is as set forth in SEQ ID NO:1.

2. The recombinant *E. coli* according to claim 1, wherein the gene IgtA encoding the ß-1,3-acetyl glucosamine transferase is expressed by using a pACYCDuet-1, pCDFDuet-1, pRSFDuet-1, pCOLADuet-1 or pETDuet-1 vector, and a gene encoding the UDP-glucose 4 epimerase and a gene encoding the ß-1,4-galactosyl transferase are co-expressed by using a pACYCDuet-1, pCDFDuet-1, pRSFDuet-1, pCOLADuet-1 or pETDuet-1 vector.

3. The recombinant *E. coli* according to claim 2, wherein the gene IgtA encoding the ß-1,3-acetyl glucosamine transferase is expressed by using the pRSFDuet-1 vector, and gene galE encoding the UDP-glucose 4 epimerase and gene Aa-β-1,4-GalT encoding the ß-1,4-galactosyl transferase are simultaneously expressed by using the pRSFDuet-1 vector.

4. The recombinant *E. coli* according to claim 2, wherein the gene IgtA encoding the ß-1,3-acetyl glucosamine transferase is expressed by using the pETDuet-1 vector, and gene galE encoding the UDP-glucose 4 epimerase and gene Aa-β-1,4-GalT encoding the ß-1,4-galactosyl transferase are simultaneously expressed by using the pRSFDuet-1 vector.

5. The recombinant *E. coli* according to claim 2, wherein the gene IgtA encoding the ß-1,3-acetyl glucosamine transferase is expressed by using the pCDFDuet-1 vector, and gene galE encoding the UDP-glucose 4 epimerase and gene Aa-β-1,4-GalT encoding the ß-1,4-galactosyl transferase are expressed by using the pETDuet-1 vector.

6. The recombinant *E. coli* according to claim 2, wherein the gene IgtA encoding the ß-1,3-acetyl glucosamine transferase is expressed by using the pACYCDuet-1 vector, and gene galE encoding the UDP-glucose 4 epimerase and gene Aa-β-1,4-GalT encoding the ß-1,4-galactosyl transferase are simultaneously expressed by using the pCOLADuet-1 vector.

7. The recombinant *E. coli* according to claim 1, wherein the nucleotide sequence of gene Aa-β-1,4-GalT encoding the ß-1,4-galactosyl transferase is as set forth in SEQ ID NO:2.

8. The recombinant *E. coli* according to claim 7, wherein gene galE encoding the UDP-glucose 4 epimerase is derived from *E. coli* K-12, and the nucleotide sequence of the gene galE is as set forth in SEQ ID NO:3.

9. The recombinant *E. coli* according to claim 8, wherein the amino acid sequence of the UDP-N-acetyl glucosamine-2-epimerase is set forth in SEQ ID NO:5, wherein the amino acid sequence of the glucosamine-6 phosphate deaminase is set forth in SEQ ID NO:6, wherein the amino acid sequence of the ß-galactosidase is set forth in SEQ ID NO:7.

10. The recombinant *E. coli* according to claim 9, wherein the *E. coli* is *E. coli* BL21 (DE3).

* * * * *